US006945935B1

(12) United States Patent
Sasse et al.

(10) Patent No.: US 6,945,935 B1
(45) Date of Patent: Sep. 20, 2005

(54) WIRELESS SLEEP MONITORING

(76) Inventors: Anthony Corry Sasse, 4A Selbourne Road, Kew VIC 3101 (AU); Stephen Garth Ratten, 17 Maramba Drive, Narre Warren VIC 3805 (AU); Jeffrey Edmond Hales, 16 Kirkham Road, Belgrave South VIC 3160 (AU)

(*) Notice: Subject to any disclaimer, the term of this patent is extended or adjusted under 35 U.S.C. 154(b) by 0 days.

(21) Appl. No.: 09/914,564

(22) PCT Filed: Mar. 3, 2000

(86) PCT No.: PCT/AU00/00149

§ 371 (c)(1),
(2), (4) Date: Nov. 15, 2001

(87) PCT Pub. No.: WO00/51488

PCT Pub. Date: Sep. 8, 2000

(30) Foreign Application Priority Data

Mar. 4, 1999 (AU) .................................... PP9022

(51) Int. Cl.[7] .................................................. A61B 5/00
(52) U.S. Cl. ..................................... 600/300; 128/903
(58) Field of Search ................................ 600/300–301, 600/484, 529, 534, 587, 595, 513; 128/204.23, 128/903, 904, 920; 340/573, 573.1, 573.4

(56) References Cited

U.S. PATENT DOCUMENTS

| 4,075,632 A | 2/1978 | Baldwin | |
| 4,531,526 A | 7/1985 | Genest | |
| 5,617,871 A * | 4/1997 | Burrows | 128/903 |
| 5,682,149 A | 10/1997 | Hofman | |
| 6,132,371 A * | 10/2000 | Dempsey et al. | 600/300 |
| 6,419,629 B1 * | 7/2002 | Balkin et al. | 600/300 |
| 6,443,890 B1 * | 9/2002 | Schulze et al. | 600/300 |
| 6,639,509 B1 * | 10/2003 | Martinez | 340/10.4 |

FOREIGN PATENT DOCUMENTS

| EP | 0 420 177 | 4/1991 |
| WO | 91/16850 | 11/1991 |

* cited by examiner

Primary Examiner—Max F. Hindenburg
Assistant Examiner—Michael C Astorino
(74) Attorney, Agent, or Firm—Stites & Harbison PLLC; Ross F. Hunt, Jr.

(57) ABSTRACT

The present invention provides a method and apparatus for physiological monitoring of a remote subject, the apparatus including: a base station having a transmission means for transmitting a reference signal; and a physiological monitoring probe connectable to the subject, the physiological monitoring probe having: receiver means for receiving the reference signal; monitoring means for monitoring the subject and generating a condition signal containing information related to a condition of the subject; modulation means for modulating the reference signal to produce a modulated reference signal containing the information contained in the condition signal; and passive retransmission means for passively retransmitting the modulated reference signal to the base station; wherein the base station has means for receiving the modulated reference signal, and means for demodulating the modulated reference signal to obtain the information related to a condition of the subject so that a condition of the subject can be monitored at the base station.

22 Claims, 4 Drawing Sheets

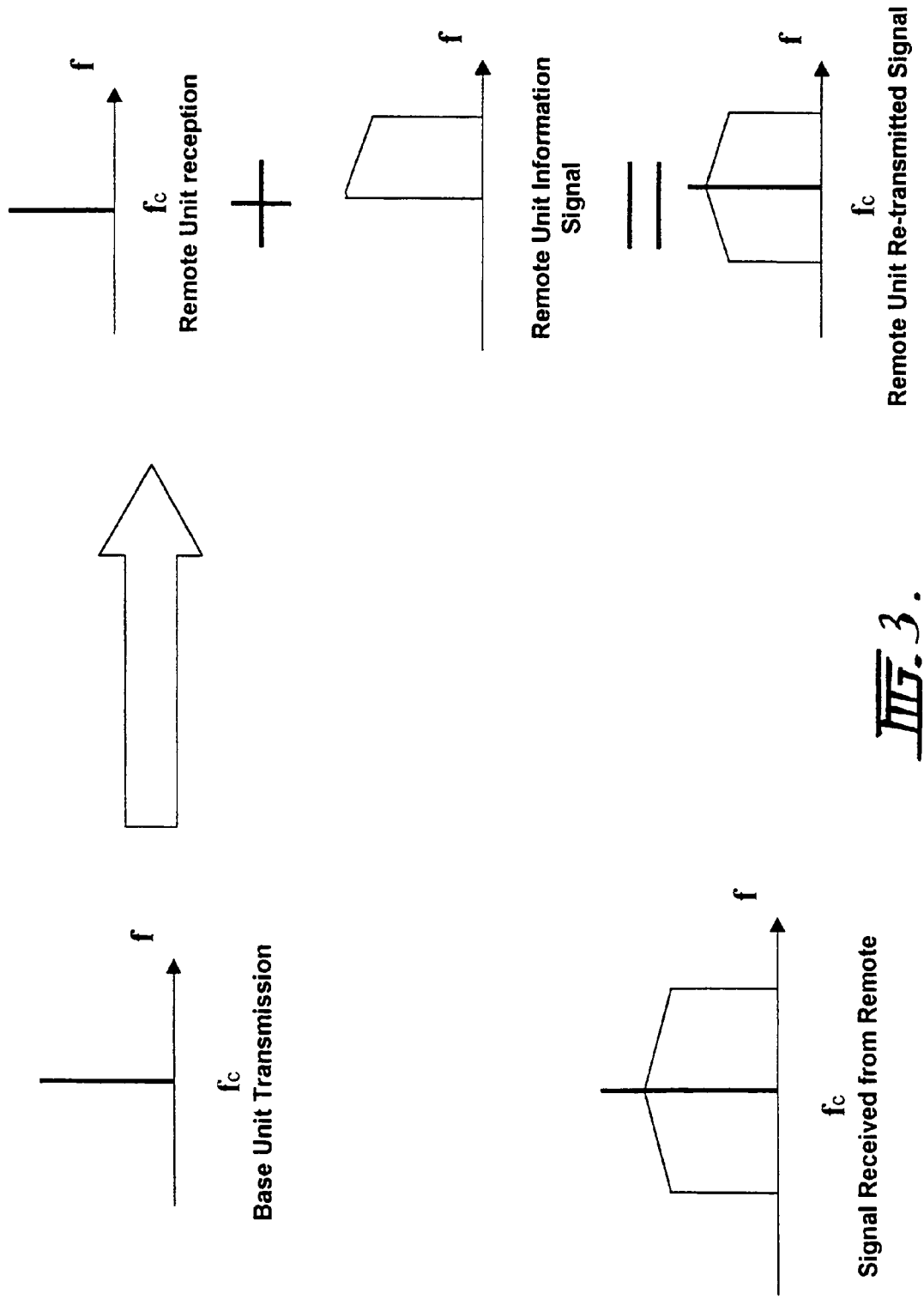

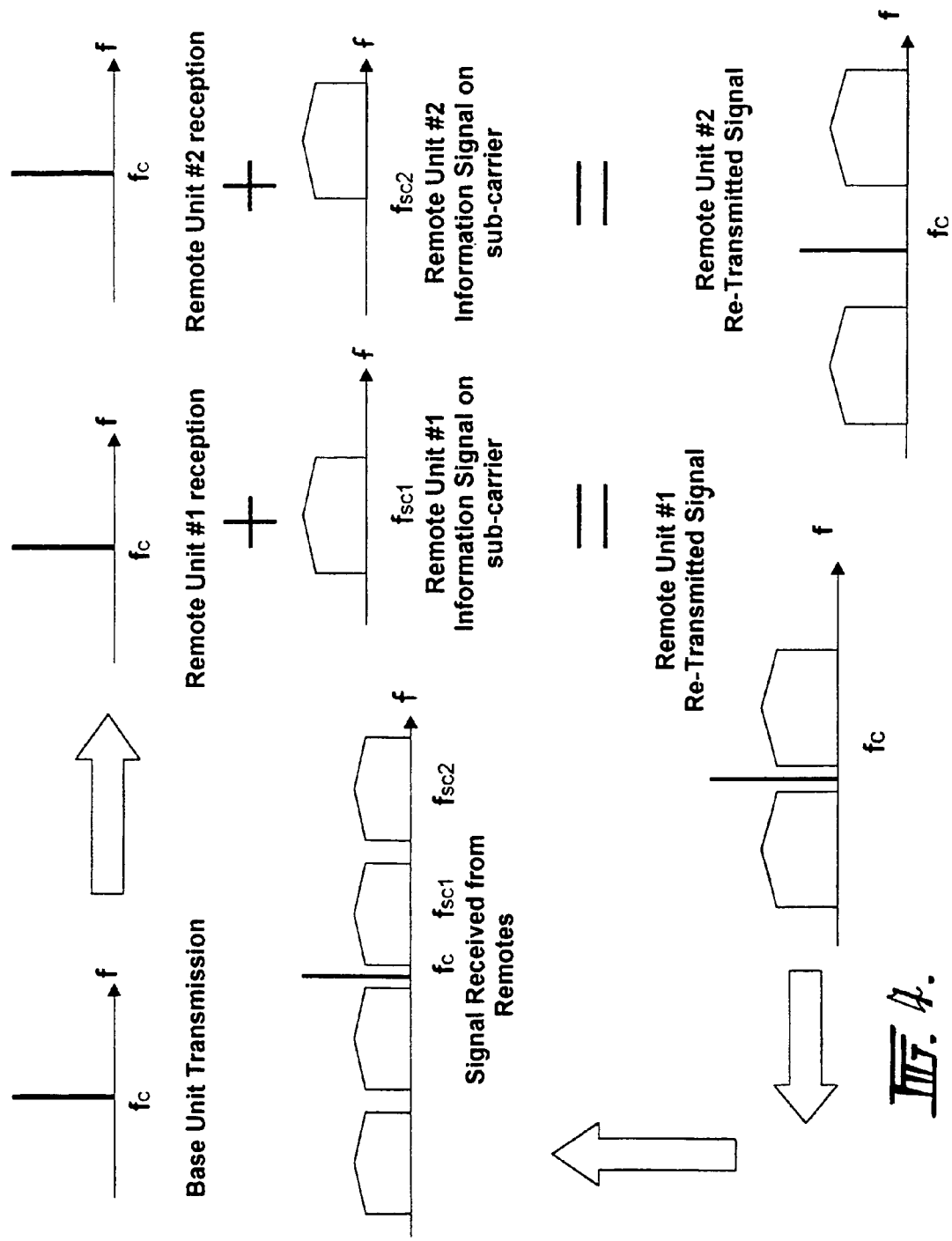

WIRELESS SLEEP MONITORING

The present invention relates to apparatus and a method for remote monitoring of the physiological state of a subject. The invention finds particular application in the area of sleep apnoea and the invention will be described in relation to sleep apnoea, however, it is to be understood that the invention is not limited to the remote monitoring of sleep apnoea.

Sleep apnoea occurs when a person stops breathing whilst asleep. While the person is asleep, tissue in the air way relaxes causing the airway to close and the person to stop breathing. Whilst the person is not breathing the oxygen level in the person's blood falls until the brain wakes up and causes the air way to tighten allowing the person to breath again. This cycle then repeats itself. People who suffer from sleep apnoea are likely to fall asleep during the day and may have other associated health problems.

If a person suffers from sleep apnoea or is suspected to suffer from sleep apnoea it is often necessary for them to spend some time sleeping in a sleep laboratory so that their sleeping patterns and sleep apnoea can be monitored. This is disruptive of the person's lifestyle. Furthermore, it is possible that the results obtained in a sleep laboratory may not accurately reflect a person's sleeping patterns merely because the person may not sleep normally in the unfamiliar surroundings of the laboratory.

Accordingly, it would be advantageous to provide apparatus which allows a person to be monitored in their own home. It would be preferable if the apparatus consumed little power so that its power source could be small and/or recharged infrequently.

Accordingly, the invention provides apparatus for physiological monitoring of a remote subject including:
  a base station having a transmission means for transmitting a reference signal; and
  a physiological monitoring probe connectable to said subject, said physiological monitoring probe having:
    receiver means for receiving said reference signal;
    monitoring means for monitoring said subject and generating a condition signal containing information related to a condition of said subject;
    modulation means for modulating said reference signal to produce a modulated reference signal containing said information contained in said condition signal; and
    passive retransmission means for passively retransmitting said modulated reference signal to said base station;
  wherein said base station has means for receiving said modulated reference signal, and means for demodulating said modulated reference signal to obtain said information related to a condition of said subject so that a condition of said subject can be monitored at said base station.

Preferably, the receiving means and passive retransmission means are a passive radio transponder.

Preferably, the monitoring means includes a physical parameter transducer.

Alternatively, the monitoring means may include a biological electrode.

The physiological monitoring means may include intermediate signal means for generating an intermediate signal derived by combining said condition signal with a fixed or varying frequency signal before modulating said reference signal.

Preferably fixed or varying frequency signal comprises a plurality of sub-carrier signals.

The intermediate signal means may be operable to convert analog and/or digital signals from the monitoring means to an intermediate signal which is used to modulate a radio frequency signal received by a passive radio transponder, so that the transponder automatically retransmits a modulated signal which contains information relating to the condition of the subject.

The base station may include analogue and/or digital outputs for outputting data.

Further, the base station may be connectable to a computer network, such as the internet or world wide web, and operable to receive input (including configuration commands) and output data via said computer network. Thus, for example, any data displayable on a video display unit provided in the base station could also be displayed on a remote video display unit in communication with the base unit over a computer network. The outputs of the base station may therefore include world wide web, WAP (Wireless Application Protocol) and/or satellite communications outputs.

The apparatus may optionally include encryption means so that said apparatus can transmit data in encrypted form. Thus, data transmitted over such a computer network (or indeed by means of the reference signal between the base station and the physiological monitoring probe) may be encrypted so that the data is secure.

The modulated reference signal may comprise a synchronous or an asynchronous data signal.

Preferably said apparatus is operable to modulate the frequency or phase of the reference signal by a Pseudo-Random Binary Sequence having an instantaneous code that determines the respective instantaneous frequency or phase.

The invention also provides a method of physiological monitoring of a remote subject including:
  transmitting a reference signal from a base station to a remote physiological monitoring probe connected to a subject;
  monitoring said subject and generating a condition signal containing information related to a condition of said subject;
  modulating said reference signal to produce a modulated reference signal containing said information contained in said condition signal;
  passively retransmitting said modulated reference signal from said biological monitoring probe to said base station; and
  demodulating said modulated reference signal to obtain said information related to a condition of said subject so that a condition of said subject can be monitored at said base station.

The method may include generating an intermediate signal derived by combining said condition signal with a fixed or varying frequency signal before modulating said reference signal.

Preferably fixed or varying frequency signal comprises a plurality of sub-carrier signals.

The method may include converting analog and/or digital signals from a subject monitoring means to an intermediate signal which is then used to modulate a radio frequency signal received by a passive radio transponder, whereby the transponder automatically retransmits a modulated signal containing information relating to the condition of the subject.

The method may include transmitting data from said base station over a computer network, such as the internet or world wide web, or inputting data (including configuration commands) over a computer network.

The method may include encrypting data to be output by said base station, and/or encrypting said modulated reference signal so that the data is secure.

The method may include transmitting said modulated reference signal as a synchronous or as an asynchronous data signal.

Preferably the method includes modulating the frequency or phase of the reference signal by a Pseudo-Random Binary Sequence having an instantaneous code that determines the respective instantaneous frequency or phase.

Preferably, the method is used to monitor sleep apnoea.

In order that the present invention may be more clearly ascertained, a preferred embodiment will now be described, by way of example, with reference to the accompanying figures in which:

FIG. 3 shows a single channel modulation scheme for the physiological monitoring apparatus of FIG. 1; and FIG. 4 shows a multichannel modulation scheme for the physiological monitoring apparatus of FIG. 1.

Figure 1:
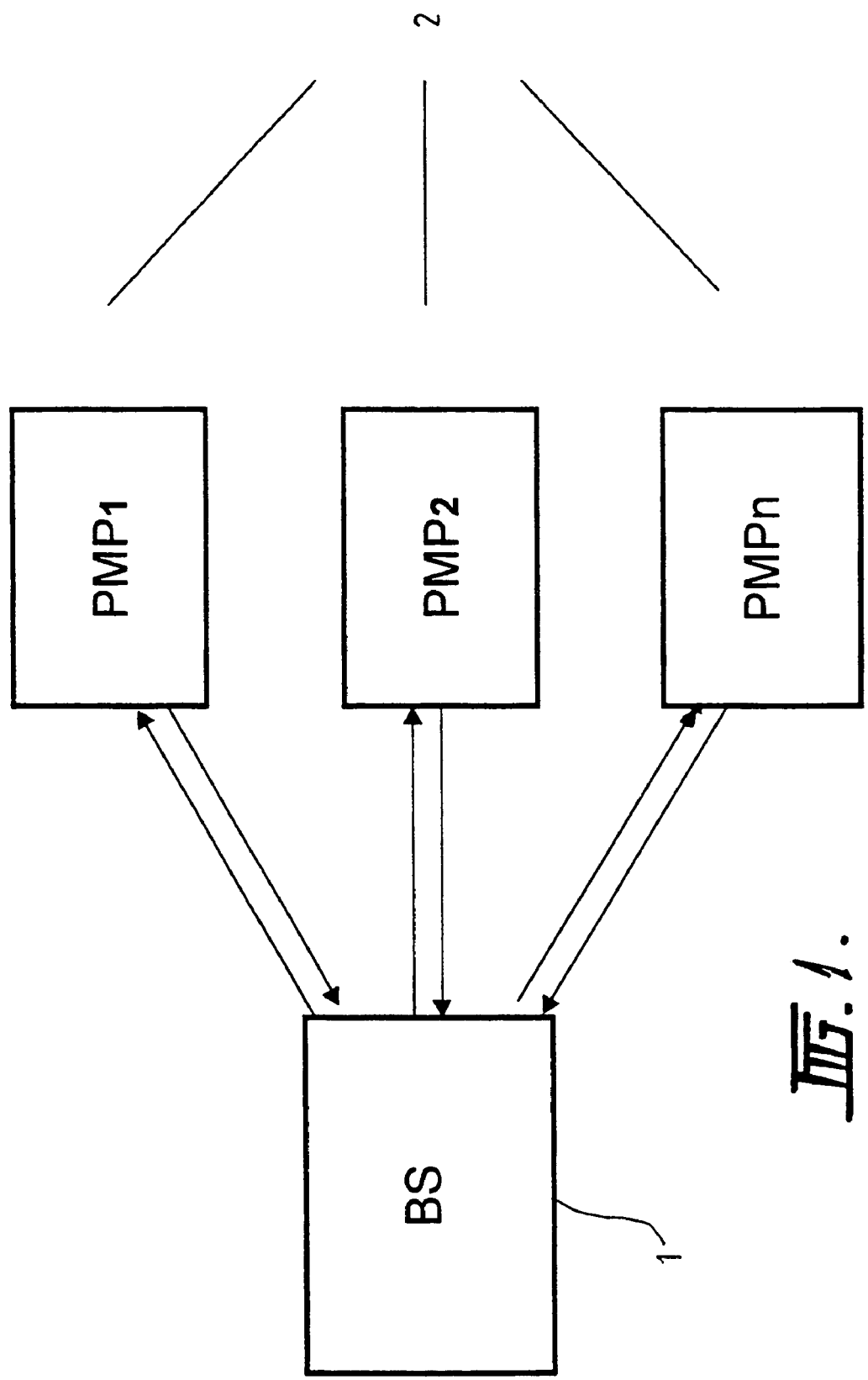
FIG. 1 is a schematic diagram showing the relationship between a base station and a plurality of physiological monitoring probes of a physiological monitoring apparatus according to a preferred embodiment of the present invention.

FIG. 1 shows a base station 1 and a plurality of physiological monitoring probes 2, located at remote locations and connected in use to individual subjects, of a physiological monitoring apparatus according to a preferred embodiment of the present invention. Hereinafter the operation of the apparatus will be described in relation to a single base station and a single physical monitoring probe, however, it should be understood that a single base station may be used to monitor a plurality of physiological monitoring probes and that the system could employ more than one base station.

The base station 1 is in radio communication with each physiological monitoring probe 2, and so clearly includes an antenna (not shown). However, the base station 1 may include multiple antennas to improve the reception of the signal from each physiological monitoring probe 2.

Figure 2:
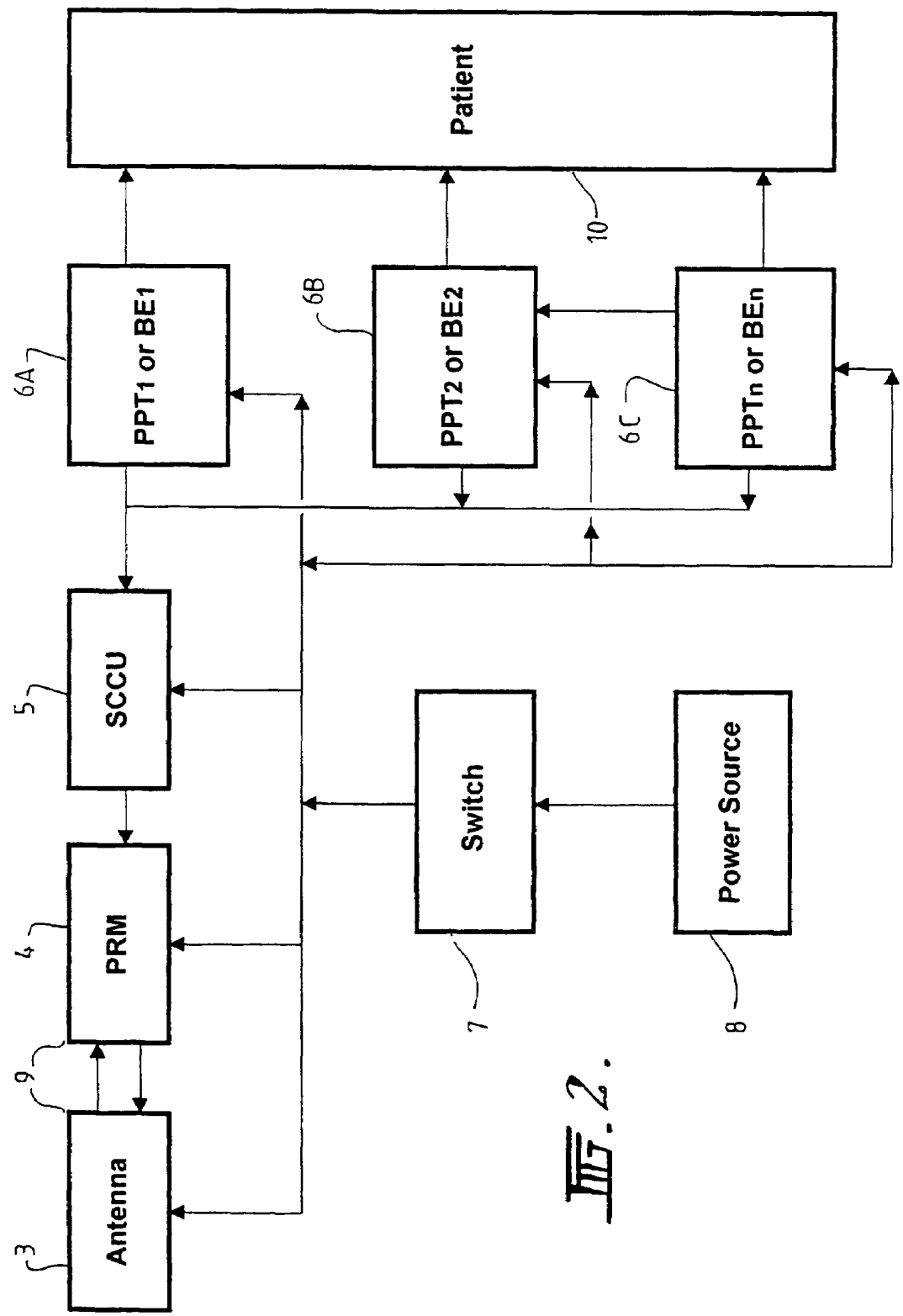
FIG. 2 is a schematic diagram of a physiological monitoring probe of the a physiological monitoring apparatus of FIG. 1.

Referring to FIG. 2, the physiological monitoring probe 2 includes a passive radio transducer 9, which itself includes an antenna 3 and a passive reflective modulator 4. When the base station 1 generates and transmits a reference signal to the physiological monitoring probe 2, the signal is received by the antenna 3 and fed to the passive reflective modulator 4. The passive radio transducer 9 also acts as a passive radio transponder and thereby provides a passive retransmission means. One or more physical parameter transducers or biological electrodes 6a, 6b and 6c provide signals to a signal conditioning and control unit 5 which relate to a condition or physical indication of a patient or subject 10.

The signal conditioning and control unit 5 combines the signals received from the physical parameter transducers and/or biological electrodes 6a, 6b, 6c into a single data stream before feeding the data stream to a modulation means in the form of a passive reflective modulator 4 where it is combined with a locally generated, fixed or varying frequency sub-carrier producing a complex intermediate signal before being combined with the radio frequency signal received from the base station 1 to produce a modulated reference signal which is passively retransmitted to the base station unit 1. In an alternative preferred embodiment, however, the physiological monitoring probe 2 optionally generates two or more sub-carrier signals each containing signals from the physical parameter transducers and/or biological electrodes. This option allows for a remote physiological monitoring probe 2 to use more than one sub-carrier to transmit the modulated reference signals, thereby improving the capacity of the physiological monitoring probe 2 to transfer information. It also allows the provision of additional error detection and correction by sending similar information via two or more sub-carriers to reduce the chance of the information being corrupted by interfering signals. The duplicated or similar information sent on each sub-carrier can be delayed in time for each sub-carrier to prevent short term bursts of interfering signals from corrupting the information.

Predominantly the energy used to generate the RF sidebands (containing the monitored information) in the modulated reference signal can be extracted from the incoming radio energy of the reference signal.

The base station 1 subsequently demodulates the modulated reference signal to extract information or data relating to the condition of the patient therefrom, whereafter the extracted data can be used for one or more purposes.

The physiological monitoring probe 2 also has a local power source 8 such as a battery which can be rechargeable or an external power source such as photovoltaic panel. The power source 8 may have an electronic power switch 7 driven by a toggling flip flop which can be toggled in response to a power switch command signal. In this way, when the physiological monitoring probe is not in use it can be disabled to save battery power. The command signal may be provided by the base station 1. Alternatively, the physiological monitoring probe could be equipped with an external accessible power switch.

The physiological monitoring probe 2 can be connected to the base station 1 or to a storage cradle (not shown) temporarily so that it may be re-programmed and/or configured or, where a rechargeable battery is provided, so that the battery can be recharged. The physical monitoring probe 2 may be configured via physical connections to the base station or alternatively radio frequency, optical, inductive, capacitive or other means may be used to pass a signal from the base station 1 to the physiological monitoring probe 2 to set various parameters for that physiological monitoring probe 2.

The apparatus my optionally include, for each physiological monitoring probe 2, a storage holder (not shown). The physiological monitoring probe 2 may be both recharged and remotely configured while in this holder.

Parameters which may be set in this configuration procedure include: channel gains; channel bandwidths; channel number; identification for the particular physiological monitoring probe; sub-carrier frequencies, and data channel rates. Information relating to the configuration of the physiological monitoring probe 2 can be included in the modulated reference signal transmitted from probe 2 so that the base station 1 can confirm that the physiological monitoring probe 2 is correctly configured.

The use of a passive reflective modulator 4 minimises power consumption by eliminating the need for carrier frequency accuracy and stability and signal generation in the passive radio transducer 9 thus extending battery life and reducing the required overall size of the physiological monitoring probe 2.

The passive reflective modulator 4 has a resonant circuit which responds to the incoming radio frequency signal (the reference signal) from the base station 1, and contains a mixing device. Typically the mixing device consists of non-linear resistive or reactive components. The mixing device is fed with a locally produced intermediate signal from the signal conditioning and control unit 5 together with the reference signal from the antenna. This signal is then impressed on the incoming reference signal which is a radio frequency signal, from the Base Station, to create a modulated reference signal which is transmitted back to the base station.

The modulation method employed may be any appropriate analog or digital modulation system using for example: angle or amplitude methods of modulation.

The intermediate signal determines the offset or offsets of the symmetrically modulated RF (radio frequency) side bands from the centre frequency of the incoming RF reference signal by utilising different sub-carrier frequencies for signals emanating from different physiological monitoring probes so that the probes can be distinguished.

FIG. 3 shows a modulation scheme for use when there is a single remote unit (i.e. a single physiological monitoring probe 2). The base station (or unit) transmits a signal at a single carrier frequency. The physiological monitoring probe 2 combines the signal received from the base unit with a locally generated intermediate signal containing information relating to the condition of a subject. This signal is subsequently passively retransmitted to the base unit where it can be decoded to extract the information. In the multichannel situation shown in FIG. 4, the carrier frequency is received at both the first and second remote unit (i.e. at two physiological monitoring probes). Each remote unit generates a different sub carrier signal containing information relating to a condition of the patient. The remote units then separately retransmit their signals to the base unit which receives the signal containing both sub carrier signals.

In a multichannel system each remote unit (ie. each physiological monitoring probe) which is within range of a base station is allocated a unique local sub carrier frequency. Hence, when more than one base unit is used the same sub carrier frequency can be assigned to more than one physiological monitoring probe or each remote unit provided that remote unit is only within range of one base station.

Where two or more independent base stations are required to operate within the range of remote units each base station's reference signal frequency can be set to different values to the others by at least a value of the typical resonant bandwidth of the remote units to prevent remote units of one base station responding to the reference signal of another base station operating in the vicinity. This utilises frequency division multiplexing principles. The remote units therefore are tuned to operate on the particular frequency of the base station they are allocated, preventing them from responding to the other base station's reference signal(s).

Similarly one base station could transmit more than one reference signal to operate with different sets of remote units while maintaining functional independence of the remote unit sets.

In a more complex multichannel variation the base station transmission signal frequency could be frequency (or phase) modulated by a Pseudo-Random Binary Sequence (PRBS) whose instantaneous code determines the frequency (or phase) at that moment.

This moves the base station transmission signal frequency across a section of spectrum in a random manner, centred on the base station transmission centre frequency (fc) (this is a variant of what is commonly called Spread Spectrum technology). By hopping or sliding the transmission frequency in this manner, the base station received signal moves synchronously with the transmission signal which greatly simplifies the method of receiving and separating received signals.

To prevent signal corruption caused by interfering in-band signals, a PRBS method reduces the chance of the information sidebands occurring at the same part of the spectrum as the interfering signals and therefore inference is minimum. The individual information channels can be extracted with conventional methods once the received signal has the PRBS effects removed from the incoming signal. This method still utilises a local intermediate signal to separate the individual channels of the remote units associated with a signal base station—i.e. unique local sub carrier frequencies are assigned to each physiological monitoring probe.

Predominantly, the physiological monitor probe does not generate any RF energy of its own but reflects the energy of the signal transmitted from the base station, back to the base station, modified with information from the patient. The only energy used in the physiological monitoring probe is that which is used to monitor the physiological condition and to combine the information signal with the intermediate sub carrier to produce the intermediate signal. Predominantly the energy for the RF sidebands themselves can be extracted from the received signal so that the energy of the reference signal is dispersed between the reflected RF carrier signal and the information side bands obtained from the intermediate signal without adding power to the RF signal from the physiological monitoring probe.

The signal conditioning control unit 5 receives analogue and digital signals from one or more biological electrodes or physical parameter transducers 6a, 6b, 6c which signals relate to physiological condition of the subject or patient. The signal conditioning control unit 5 converts these individual signals into a single digital or analogue data stream which it feeds to its data modulator along with a locally generated local oscillator signal. The data modulator combines the local oscillator signal with the data stream producing an output comprising one or more sidebands which are centred on a sub-carrier derived from the locally produced oscillator signal. The information (data) signal which is modulated onto the sub-carrier is called the intermediate signal and is passed to the passive reflective modulator 4. The sub-carrier itself may have a spread spectrum to allow multiple remote units to modulate their respective information signals on the one sub-carrier frequency. The passive reflective modulator 4 combines the intermediate signal received from the signal conditioning and control unit 5 with the incoming reference signal and passes the modulated reference signal back to the antenna 3 of the passive radio transducer 9 which re-radiates the signal across the radio path to the base station 1. The intermediate signal from the signal conditioning control unit 5 may also include other information such as: that required for forward error correction or other data detection or correction methods; framing codes; data compression; delta modulation; an identification number; etc.

Preferably the antenna 3 is miniaturised. However, it may be either internal or external to each physiological monitoring probe. In a preferred embodiment the antenna is integrated with the leads to the biological electrodes or physical parameter transducers in order to reduce the required size of the unit. Depending on the application, different physical parameter transducers or biological electrodes may be used. That is to say, different transducers or electrodes may be used depending on what condition of the patient is being monitored. The transducers or electrodes need not necessarily be formed integrally with the physiological monitoring probe 2. For example, varying numbers of electrodes or transducers could be plugged in via leads to suitable galvanic connections in the surface of the physiological monitoring probe 2. In such an arrangement, separate power sources can provide for each of the transducers or probes in order to reduce the burden on the power source 8 which is used to drive the passive radio transducer 9.

The base station 1 has one or more radio receivers, a power supply which may be either mains power or a battery, one or more data demodulators, one or more data processing modules, a variety of external interfaces such as indicator lights and displays and data inputting means such as keyboard or buttons. Optionally, the base station 1 may be connectable to a computer network, such as the internet, so that its outputs can be monitored at locations other than that of the base station 1, and so that data can be entered into the base station 1 from those locations.

The radio receiver has means for pre-processing the received signal before it is fed to the data demodulator. The radio receiver also includes one or more radio frequency amplifiers, one or more local oscillators, one or more mixers, one or more filters, one or more attenuators, one or more matching networks and one or more intermediate frequency amplifiers.

The data demodulator uses a demodulation method which complements the method used to modulate the reference signal in the physiological monitoring probe 2.

The data processing module receives data from the demodulator and interprets this data so that individual data channels can be separated which relate to different conditions of the person. Error detection can be performed on the data at this stage and the data can be sent to the external interfaces or stored in a data storage device or both.

The base station also includes a control module which is responsible for the overall operation of the base station. The control module configures and/or controls and/or operates a radio receiver for frequency, gain, RF power, control of the data demodulator configuration and/or operation. Indicators and displays are also controlled by the control module. For example the control module may monitor the data from the data module until it detects a particular piece of data or pattern of data which indicates the need to sound an alarm. For example, if the device is being used to monitor sleep apnoea an alarm may be sounded if the person stops breathing for an extended period of time. Connection of the base station 1 or a physiological monitoring probe 2 via an interface to external devices allows, in one embodiment, the detected condition to activate intervention equipment to reduce or prevent the condition from occurring for dangerous periods.

Other external interfaces may be utilised which display and/or record monitored physiological data for diagnosis.

The base station 1 can also include means for indicating faults such as loss of received signal from the physiological monitoring probe 2.

The physiological monitoring apparatus hereinbefore described can be used for a number of applications such as the monitoring of the condition of a patient and alternatively as a vigilance monitor for operators of vehicles or equipment. While the physiological monitoring apparatus has been described in relation to monitoring sleep apnoea, it would be used to monitor any number of physiological conditions of a subject where it is appropriate that the subject be monitored remotely. Physical conditions which could be monitored include, but are not limited to:

pulse rate, blood pressure (in real time or as an average over time), temperature (external and internal), humidity (internal and external), skin conductivity, EEG, EMG, ECG, flexure, movement, skin colour changes, pulse oximeter, plethysmography, airflow (nasal and oral) and fluid flow.

Depending on what monitoring is being undertaken, a different set of conditions can be monitored. For example, vigilance monitoring of drivers will require the monitoring of a different range of physical conditions to sleep apnoea. Furthermore, in some circumstances it may be helpful to monitor some aspects of the environment in which the subject is located, for example: temperature, levels of gases such as oxygen, the amount of light to which the subject is exposed, etc. These aspects can be monitored by the physiological monitoring probe attached to the subject, although in some circumstances it may be appropriate to use separate monitoring equipment.

The system can incorporate further features and has additional advantages as discussed below.

The simplicity of the system allows it to be small in size have low weight, low cost and consume less power. The consumption of less power allows batteries to be of a small size and for them to last for the duration of a monitoring session. If a patient is under constant monitoring batteries can be changed or recharged at longer intervals. The small size also allows the physiological monitoring probe to be worn as a small pad or patch with the sensors in the form of biological electrodes or physical parameter transducers 6a, 6b, or 6c being attached or integral to the physiological monitoring probe. Because the system is wireless it does not encumber the patient. Similarly, because the system can be light in weight, it will not encumber the patient. Another feature of the system can be that the transmission power can be below licensing limits therefore obviating the need for radio frequency licensing of the system. As discussed above, the multichannel nature of some embodiments of the system allows there to be several remote units from a signal RF channel and allows more remote units of physiological monitoring probes to be added to the system at any time. Another advantage of the system is that it allows the patient to move around easily because no cables have to be disconnected. With an appropriate design and choice of RF frequency the electrode wires of the physiological monitoring probe 2 can be combined with the antenna 4 in order to reduce the size of the device. Similarly the antenna may be made integral to the physiological monitoring probe itself. There is also potential for the device to be modified so that it can be implanted in a patient's body.

Again, as discussed above, the present system is not limited to monitoring of sleep apnoea and can be used for various physiological and physical monitoring processes. Also, as previously discussed the system is not limited to use on patients and as such can be used in other circumstances where it is necessary to monitor a subject. The system could also be used to monitor animals.

Modifications within the spirit and scope of the invention may readily be effected by a persons skilled in the art, so it is to be understood that this invention is not limited to the particular embodiments described by way of example hereinabove.

What is claimed is:

1. Apparatus for physiological monitoring of a remote subject including:
    a base station having a transmission means for transmitting a reference signal; and at least one physiological monitoring probe connectable to said subject, said physiological monitoring probe or probes having:

receiver means for receiving said reference signal;

monitoring means for monitoring said subject and generating a condition signal containing information related to a condition or conditions of said subject;

intermediate signal means for generating an intermediate signal derived by combining said condition signal with a fixed or varying frequency sub-carrier signal before modulating said reference signal;

modulation means for modulating said reference signal with said intermediate signal to produce a modulated reference signal containing said information contained in said condition signal; and passive retransmission means for passively retransmitting said modulated reference signal to said base station;

wherein said base station has means for receiving said modulated reference signal, and means for demodulating said modulated reference signal to obtain said information related to one or more conditions of said subject so that at least one condition of said subject is available to be monitored at said base station, and said base station includes means for varying the frequency or phase of the reference signal so that said reference signal is a spread spectrum reference signal.

2. Apparatus as claimed in claim 1, wherein said receiving means and passive retransmission means are a passive radio transponder.

3. Apparatus as claimed in claim 1, wherein said monitoring means includes a physical parameter transducer.

4. Apparatus as claimed in claim 1, wherein said monitoring means includes a biological electrode.

5. Apparatus as claimed in claim 1, wherein said intermediate signal means is operable to convert analog and/or digital signals from the monitoring means to an intermediate signal which is used to modulate a radio frequency signal received by a passive radio transponder, so that the transponder automatically retransmits a modulated signal which contains information relating to the condition of the subject.

6. Apparatus as claimed in claim 1, wherein said passive radio transponder uses a plurality of intermediate signals to modulate a radio frequency reference signal.

7. Apparatus as claimed in claim 1, wherein said base station includes analog and/or digital outputs for outputting data.

8. Apparatus as claimed in claim 1, wherein said base station is connectable to a computer network, and operable to receive input and output data via said computer network.

9. Apparatus as claimed in claim 1, including encryption means so that said apparatus can transmit and/or receive data in encrypted form.

10. Apparatus as claimed in claim 1, wherein said condition signal includes a synchronous or an asynchronous data signal.

11. Apparatus as claimed in claim 1, wherein said base station is operable to vary the frequency or phase of the reference signal by a continuously varying signal having an instantaneous value that determines the respective instantaneous frequency or phase.

12. Apparatus as claimed in claim 11 in which the continuously varying signal is derived from a Pseudo-Random Binary Sequence.

13. A method of physiological monitoring of a remote subject including:

transmitting a reference signal from a base station to at least one remote physiological monitoring probe connected to a subject;

varying the frequency or phase of said reference signal so that said reference signal is a spread spectrum reference signal;

monitoring said subject and generating a condition signal containing information related to a condition or conditions of a said subject;

generating an intermediate signal derived by combining said condition signal with a fixed or varying frequency sub-carrier signal;

modulating said reference signal with said intermediate signal to produce a modulated reference signal containing said information contained in said condition signal;

passively retransmitting said modulated reference signal from said biological monitoring probe to said base station; and demodulating said modulated reference signal to obtain said information related to the condition or conditions of said subject so that the condition or conditions of said subject can be monitored at said base station.

14. A method as claimed in claim 13, wherein said intermediate signal is one of a plurality of intermediate signals, and said fixed or varying frequency sub-carrier signal is one of a plurality of sub-carrier signals, each corresponding to a respective one of said plurality of intermediate signals.

15. A method as claimed in claim 13 further including converting analog and/or digital signals from a subject monitoring means to the intermediate signal which is then used to modulate a radio frequency signal received by a passive radio transponder, whereby the transponder automatically retransmits a modulated signal containing information relating to the condition of the subject.

16. A method as claimed in claim 13, including transmitting data from said base station over a computer network, and/or inputting data over a computer network.

17. A method as claimed in claim 13, including encrypting data to be output by said base station, and/or encrypting said modulated reference signal.

18. A method as claimed in claim 13, including transmitting said condition signal as a synchronous or an asynchronous data signal.

19. A method as claimed in claim 13, including varying the frequency or phase of the reference signal by a continuously varying signal having an instantaneous value that determines the respective instantaneous frequency or phase.

20. A method as claimed in claim 19 in which the continuously varying signal is derived from a Pseudo-Random Binary Sequence.

21. A method as claimed in claim 13, wherein said method is used to monitor sleep apnoea.

22. Apparatus as claimed in claim 1, wherein said base stations is also operable to use a fixed frequency reference signal.

* * * * *